US009855149B2

(12) United States Patent
Bertollo et al.

(10) Patent No.: US 9,855,149 B2
(45) Date of Patent: Jan. 2, 2018

(54) INTERBODY FUSION DEVICE

(71) Applicant: Empire Technology Development LLC, Wilmington, DE (US)

(72) Inventors: Nicky Bertollo, Kirribilli (AU); William R. Walsh, Maroubra (AU); Matthew H. Pelletier, Matraville (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 590 days.

(21) Appl. No.: 14/488,910

(22) Filed: Sep. 17, 2014

(65) Prior Publication Data

US 2016/0074173 A1    Mar. 17, 2016

(51) Int. Cl.
*A61F 2/44* (2006.01)
*A61F 2/30* (2006.01)

(52) U.S. Cl.
CPC .... *A61F 2/4455* (2013.01); *A61F 2002/3023* (2013.01); *A61F 2002/30062* (2013.01); *A61F 2002/3092* (2013.01); *A61F 2002/3093* (2013.01); *A61F 2002/30176* (2013.01); *A61F 2002/30266* (2013.01); *A61F 2002/30433* (2013.01); *A61F 2002/30462* (2013.01); *A61F 2002/30471* (2013.01);
(Continued)

(58) Field of Classification Search
CPC ........ A61F 2002/448; A61F 2002/4485; A61F 2/4455
See application file for complete search history.

(56) References Cited

U.S. PATENT DOCUMENTS

2003/0065396 A1* 4/2003 Michelson .......... A61F 2/30744
623/17.15
2005/0177235 A1   8/2005 Baynham et al.
(Continued)

FOREIGN PATENT DOCUMENTS

WO   2008134515 A1   11/2008
WO   2011142761 A1   11/2011

OTHER PUBLICATIONS

"Interbody Cages for Spine Fusion," Accessed at http://web.archive.org/web/20131114112924/http://www.spine-health.com/treatment/spinal-fusion/interbody-cages-spine-fusion, Accessed on Jul. 16, 2014, pp. 2.

*Primary Examiner* — Andrew Yang
(74) *Attorney, Agent, or Firm* — Turk IP Law, LLC

(57) ABSTRACT

Technologies are generally provided for a spinal fusion device to achieve interbody fusion and maintain intervertebral spacing. The spinal fusion device includes at least two wedge-shaped intervertebral implants (IVIs) configured to be inserted between adjacent vertebrae, such that a thin end of each IVI is positioned toward a midline of the vertebrae, and a thick end of each IVI is positioned substantially flush with outer surfaces of the vertebrae. A lower surface of a superior vertebral body and an upper surface of an adjacent inferior vertebral body are resected to accommodate the IVIs, and a portion of an intervertebral disc (IVD) is also removed to facilitate insertion of the IVIs. The IVIs are inserted in substantially opposite positions to each other between the vertebrae, and an interconnecting member is inserted to connect the IVIs. The interconnecting member passes through residual IVD to stabilize the IVIs in position between the vertebrae.

19 Claims, 6 Drawing Sheets

(52) U.S. Cl.
CPC .............. *A61F 2002/30538* (2013.01); *A61F 2002/30616* (2013.01); *A61F 2002/30787* (2013.01); *A61F 2002/448* (2013.01); *A61F 2002/4475* (2013.01); *A61F 2310/00011* (2013.01); *A61F 2310/00179* (2013.01); *A61F 2310/00359* (2013.01)

(56) References Cited

U.S. PATENT DOCUMENTS

2010/0076559 A1  3/2010  Bagga et al.
2011/0144755 A1  6/2011  Baynham et al.

\* cited by examiner

INTERBODY FUSION DEVICE

BACKGROUND

Unless otherwise indicated herein, the materials described in this section are not prior art to the claims in this application and are not admitted to be prior art by inclusion in this section.

Interbody fusion is a surgical procedure to repair a degenerative intervertebral disc, spondylolisthesis, intervertebral disc herniation, kyphosis, and lordosis. Common methods of interbody fusion include an interbody fusion device, a synthetic bone graft material, an autograft, and an allograft, which allow for fusion between adjacent vertebrae, limiting motion and the pain derived from it.

An intervertebral fusion cage is a commonly used surgical interbody fusion device, which is generally used to fuse two or more vertebrae. The intervertebral fusion cage is typically made from titanium cylinders, which are placed in the disc space between vertebrae. The fusion cage is typically porous and allows the bone graft, the autograft, or the allograft to grow from the vertebral body through the cage and into the next vertebral body. The intervertebral fusion cage is typically placed in the anterior lumbar interbody fusion (ALIF) through a minilaparotomy, as an endoscopic approach is difficult. However, both the posterior and anterior surgical approach are difficult, as the spinal cord is obstructive in the posterior approach and multiple major organs and arteries are obtrusive in the anterior approach. The intervertebral fusion cage also obscures post-operative assessment, such as x-ray assessment, due to the metal in the disc space.

Additionally, possible complications from the surgery include injury to the spine or nerves, injury to the blood vessels causing bleeding, migration of the implant, infection, and blood clots.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

According to some examples, the present disclosure describes a spinal fusion device to achieve interbody fusion and maintain intervertebral spacing. The spinal fusion device may include a substantially wedge-shaped first intervertebral implant and a substantially wedge-shaped second intervertebral implant (IVI) configured to be inserted bilaterally between a first vertebra and second vertebra displacing at least a portion of an intervertebral disk (IVD) between the first and second vertebrae. The thin end of each IVI may be positioned toward a midline of the first and second vertebrae. The thick end of each IVI may be positioned to be substantially flush with outer surfaces of the first and second vertebrae.

According to other examples, the present disclosure also describes a method to achieve interbody fusion. The method may include inserting first and second intervertebral implants (IVIs). The first and second intervertebral implants may each be substantially wedge-shaped and tapered from a thick end to a thin end, between first and second vertebrae displacing at least a portion of an intervertebral disk (IVD) between the first and second vertebrae. The method may additionally include positioning the thin end of each IVI toward a midline of the first and second vertebrae such that the thick end of each IVI may be positioned to be substantially flush with outer surfaces of the first and second vertebrae.

According to further examples, the present disclosure may also describe a method of forming a spinal fusion device to achieve interbody fusion. The method may comprise configuring first and second intervertebral implants (IVIs) to have a substantially wedge-shape such that each IVI may be tapered from a thick end to a thin end. The first and second IVIs may be configured to be inserted between first and second vertebrae displacing at least a portion of an intervertebral disk (IVD) between the first and second vertebrae. The thin end of each IVI may be positioned toward a midline of the first and second vertebrae. The thick end of each IVI may be positioned to be substantially flush with outer surfaces of the first and second vertebrae. The method may additionally comprise adapting at least one interconnecting member configured to connect the first IVI with the second IVI and to pass through a residual IVD to stabilize the first and second IVIs in position between the first and second vertebrae.

According to some examples, the present disclosure also describes a system for achieving interbody fusion. The system may comprise a substantially wedge-shaped first and second intervertebral implants (IVIs), which may be configured to be inserted bilaterally between a first and second vertebrae displacing at least a portion of an intervertebral disk (IVD) between the first and second vertebrae. A thin end of each IVI may be positioned toward a midline of the first and second vertebrae. A thick end of each IVI may be positioned to be substantially flush with outer surfaces of the first and second vertebrae. The system may additionally comprise an interconnecting member configured to connect the first IVI with the second IVI and may be configured to pass through the residual IVD to stabilize the first and second IVIs in position between the first and second vertebrae.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
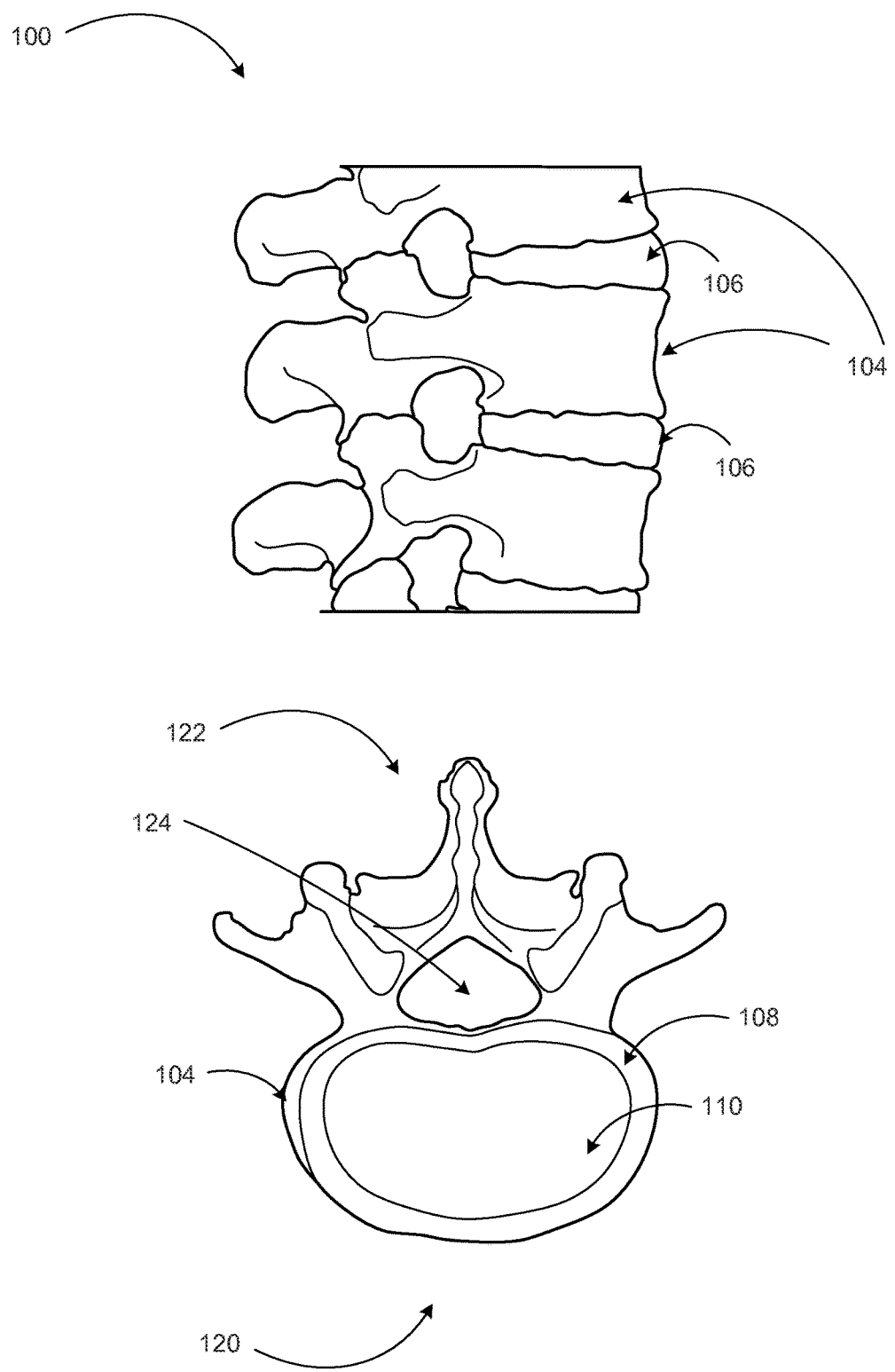
FIG. 1 illustrates an example spinal column and cross section of a vertebral body.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to compositions, methods, apparatus, systems, and/or devices related to providing an interbody spinal fusion device.

Briefly stated, technologies are generally provided for a spinal fusion device to achieve interbody fusion and maintain intervertebral spacing. The spinal fusion device may include at least two wedge-shaped intervertebral implants (IVIs) configured to be inserted between adjacent vertebrae, such that a thin end of each IVI may be positioned toward a midline of the vertebrae, and a thick end of each IVI may be positioned substantially flush with outer surfaces of the vertebrae. A lower surface of a superior vertebral body and an upper surface of an adjacent inferior vertebral body may be resected to accommodate the IVIs, and a portion of an intervertebral disc (IVD) may be also removed to facilitate insertion of the IVIs. The IVIs may be inserted in substantially opposite positions to each other between the vertebrae, and an interconnecting member may be inserted to connect the IVIs. The interconnecting member passes through residual IVD to stabilize the IVIs in position between the vertebrae.

FIG. 1 illustrates an example spinal column and cross section of a vertebral body, arranged in accordance with at least some embodiments as described herein.

An example human spinal column 100 includes 33 vertebrae, including 24 articulating vertebrae in upper regions of the spine (i.e. cervical, thoracic, and lumbar regions), and nine fused vertebrae in a lower region below the lumbar region forming a sacrum and a coccyx of the spine. The vertebrae are separated by intervertebral discs 106 that provide separation and cushioning between the vertebrae. The vertebrae provide for muscle connection to enable movement of the spine, and to allow the spine to support the weight of the upper body. The vertebral column also provides protection for the spinal cord.

An example vertebra includes an anterior portion 120, or a vertebral body 104, and a posterior portion 122, which includes lamina, pedicles and facet joints. The anterior portion 120 and posterior portion 122 together enclose a foramen 124 that forms a canal for protection of the spinal cord. The body 104 is composed of hard cortical bone on the outside which forms a rim 108 around a circumference of the body 104, and less dense, or spongy, cancellous bone 110 on the inside. The intervertebral discs 106 are sandwiched between adjacent vertebral bodies and are attached to the rims 108 of each vertebral body 104 via a bony endplate. The intervertebral discs 106 are soft, compressible discs that separate the vertebral bodies 104, acting as shock absorbers for the spine, and allowing the spine to flex, bend, and twist. Over time, the intervertebral discs 106 can break down, or degenerate, putting pressure on the spinal cord and nerves, which can lead to pain and can affect nerve function.

A spinal fusion is a procedure designed to alleviate symptoms of disc degeneration and other disc issues, including herniation, spondylolisthesis, kyphosis, and lordosis, for example. The spinal fusion may involve causing two or more adjacent vertebrae to permanently fuse together in order to eliminate motion in the fused segment of the spine, and thereby decrease and/or eliminate the back pain created by the motion of the spine. Some existing methods to achieve spinal fusion may include a fusion cage, as discussed above. The fusion cage may be a rectangular prism with a central passage which can be filled with bone graft, and fusion is achieved by guided bone growth through the central passage. Other techniques may involve placing bone graft material between the vertebrae, and employing metal plates, screws or rods to hold the vertebrae together while the bone graft fuses the vertebrae together. Many existing techniques have proved to be problematic, in that it may be difficult to insert and position the devices due to the anatomic structure of the area, and additionally existing techniques may be associated with high rates of clinical failure requiring revision surgery due to implant subsidence (for example, protrusion into the softer cancellous bone of the vertebral body), and due to localized high compressive stresses imparted to the endplates of the vertebral bodies by the devices.

A system according to embodiments may provide an interbody fusion device to achieve spinal stability and fusion between adjacent vertebral bodies and to maintain intervertebral spacing. Spinal stability and maintained vertebral spacing may be achieved by a wedging effect caused by the interbody fusion device, and eventual spinal fusion may be promoted via bony ingrowth and ongrowth onto a specialized surface of the interbody fusion device. The location of the interbody fusion device at a periphery of the vertebrae, as opposed to a central midline location, may provide mechanical stability and advantage over existing techniques and may reduce an incidence of implant subsidence. For example, compressive loads of the spine may be applied through the interbody fusion device via the cortical bone rim 108 of the body 104, as opposed to the endplates bearing the compressive loads, which may help reduce the incidence of implant subsidence.

Figure 2:
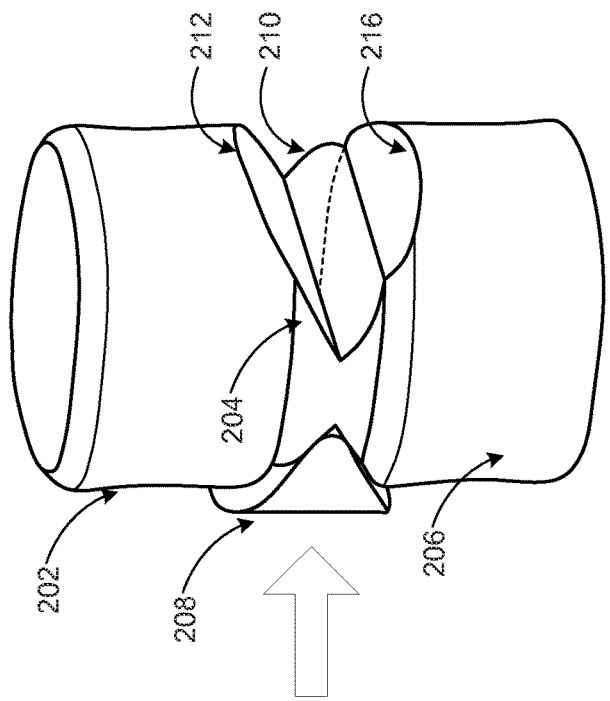
FIG. 2 illustrates an example interbody fusion device inserted between two vertebral bodies.
Figure 2:
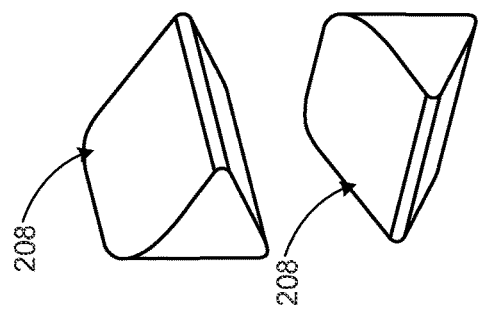
Figure 2:
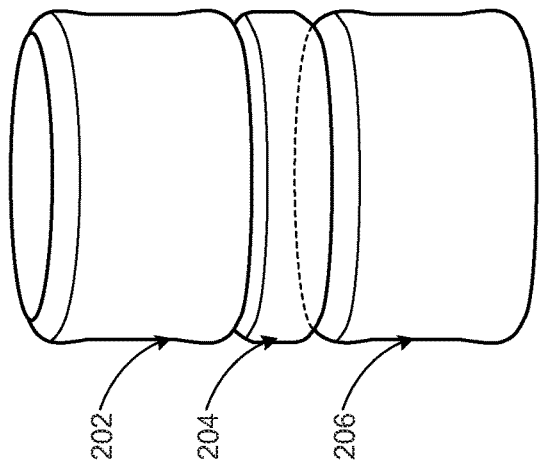

FIG. 2 illustrates an example interbody fusion device inserted between two vertebral bodies, arranged in accordance with at least some embodiments as described herein.

As previously discussed, an intervertebral disc 204 may be located between adjacent vertebral bodies (202, 206). Due to disc degeneration or other disc complications, it may be desirable to fuse the adjacent vertebral bodies (202, 206). In a system according to embodiments, an interbody fusion device may be employed to achieve fusion between the adjacent vertebral bodies while maintaining a vertebral spacing.

In an example embodiment, the interbody fusion device may include at least two substantially wedge-shaped intervertebral implants (IVIs) 208. An example wedge-shaped IVI may resemble a triangle prism with a tapered shape from a thick end to a thin end, and have a constant slope from the thin end to the thick end. The at least two substantially wedge-shaped IVIs 208 may be inserted bilaterally between a superior vertebra 202 and an inferior vertebra 206 such that the IVIs 208 are positioned substantially opposite and parallel to each other on lateral aspects of the spine. In another embodiment, the IVIs 208 may be positioned at anterior and posterior aspects of the spine. Furthermore, multiple IVIs 208 may be inserted between adjacent vertebrae at opposing positions around the periphery of the vertebrae. For example, four IVIs 208 may be placed at two lateral positions, an anterior position, and a posterior position. In yet other embodiments, the inserting position may be determined based on the patient's condition being treated, for example, when there is an abnormal curvature that also needs to be fixed or the disc is particularly worn/weak at one point. In some cases, three IVIs may be used too.

In an example embodiment, when the IVIs 208 are in position between the vertebrae such that the IVIs 208 are in a substantially opposite and parallel position to each other, the thin end of each IVI may be positioned next to each other near a midline of the vertebrae, and the thick end of each IVI may be positioned at the periphery of the vertebrae. The thick end of each IVI may be substantially flush with the periphery of the vertebrae. The change in thickness of the thin end to the thick end of each IVI may be selected to match an anatomy of an intervertebral distance between adjacent vertebrae in order to maintain a natural and/or desired intervertebral spacing between the adjacent vertebrae. Additionally, after insertion of the IVIs, a slope from the thin end to the thick end of the IVIs may be adjustable to increase the intervertebral spacing between the adjacent vertebrae.

In an alternative embodiment, the IVIs may be inserted between the first and second vertebrae such that the thick end of each IVI may be located towards a midline of the vertebrae and the thin end may be substantially flush with the outer surface. An appropriate corresponding resection of the inferior and superior surfaces of the first and second vertebrae may be made to accommodate insertion of the IVIs with the thick end toward the midline of the vertebrae.

In an example embodiment, before insertion of the IVIs 208, at least a portion the intervertebral disc 204 may be removed 210 to accommodate insertion of the IVIs 208 between the first and second vertebrae. Additionally, a portion of the first and second vertebrae may be resected to accommodate insertion of the IVIs 208 in intervertebral space between the first and second vertebrae. The resected portions may resemble chamfers. For example, a lower surface 212 of a superior vertebra 202 and an upper surface 216 of an adjacent inferior vertebra 206 may be resected to accommodate insertion of the IVIs 208. The resected portions of the vertebrae may provide a mechanical advantage by providing a greater surface area of bone contact with the IVIs 208 to aid in integration and fusion. The resected portion of the bone also may stimulate a healing response which may result in the new formation of bone and associated ongrowth and ingrowth through the IVIs 208 to achieve fusion.

A slope of the resected portions from an interior portion to an exterior portion of the vertebrae may be configured to match a slope of the wedge-shaped IVIs 208 from the thin end to the thick end. In some embodiments, the vertebrae may not be resected prior to insertion of the IVIs 208, and the slope of the natural anatomy of the vertebrae from an interior portion to an exterior portion of the vertebrae without resection may be configured to match a slope of the wedge-shaped IVIs 208 from the thin end to the thick end. Additionally, a lateral cross section of upper surfaces of the IVIs 208 may be configured to match a lateral cross section of a lower surface of the superior vertebra 202, and a lateral cross section of lower surfaces of the IVIs 208 may be configured to match a lateral cross section of an upper surface of the adjacent inferior vertebra 206. In an example scenario, the natural anatomy of a patient may be determined from a pre-operative Computed Tomography (CT) and Magnetic Resonance Imaging (MRI), and patient-specific IVIs may be manufactured using rapid prototyping to match the natural anatomy of the patient. The IVIs may be manufactured to match geometry of adjacent vertebrae, such that the IVIs may replace a diseased excised intervertebral disc.

In a system according to embodiments, the vertebrae may be resected to match a desired curvature (i.e. kyphosis and/or lordosis) of the spine, and a uniform shape of the IVIs 208 having a constant slope. Example IVIs 208 having a uniform shape have a constant slope that does not vary from anterior to posterior direction, or in a medial to lateral direction. In an example scenario, a desired curvature may be induced preoperatively prior to resection, and the vertebrae may be resected such that a slope of the resection may match the uniform slope of the IVIs 208 selected for insertion. The slope of the resection planes may be substantially symmetrical. The resection planes may be created in superior and inferior surfaces of upper and lower vertebrae, and the IVIs 208 exhibiting a slope from a thick lateral end to a thin central end may be utilized where there may be no change in anterior to posterior slope of the IVIs. In another embodiment, the vertebrae may be resected while the patient is in a neutral position, and IVIs 208 having a slope matching a desired curvature of the spine may be selected. A desired curvature may be induced after the resection planes are created by modifying an anterior-posterior (front to back) slope of the interbody fusion device including the first and second IVIs in situ, such that the interbody fusion device exhibits a variable slope in two planes. For example, the interbody fusion device may have a slope from thin to thick dimensions in two approximately perpendicular planes. Additionally, a desired curvature may be induced by selectively modifying the slope of the IVIs 208 in anterior to posterior and medial to lateral directions.

In a system according to embodiments, the IVIs 208 may be composed from various bio-compatible materials including polymer materials, metal materials, and ceramic materials. The IVIs 208 may also be composed from a bio-absorbable material such that after the vertebrae achieve fusion, the IVIs 208 may be resorbed by the body over time. Additionally, in order to promote bony ingrowth and ongrowth to facilitate fusion, a bone graft substitute or similar biological material may be incorporated with the IVIs 208. The IVIs 208 may be configured to be substantially porous to promote bone growth between the adjacent vertebrae through the IVIs 208. An example bone graft material may be an autograft, an allograft, a bone graft substitute, and a bone morphogenic protein. The bone graft may serve as a foundation to enable new bone to form and grow to fuse the vertebrae together. In an example scenario, the bone graft may be inserted between the vertebrae with the IVIs 208, and after insertion, the bone graft may promote ingrowth and ongrowth of new bone through the porous IVIs 208 to achieve fusion of the vertebrae across the IVIs 208. Furthermore, upper and lower surfaces of the IVIs 208 may be treated prior to insertion in order to create an osteoconductive surface to promote bone growth with the IVIs 208. Additionally, the upper and lower surfaces may be topographically treated prior to insertion to configure the IVIs 208 to resist shear loading and expulsion during initial insertion.

Figure 3:
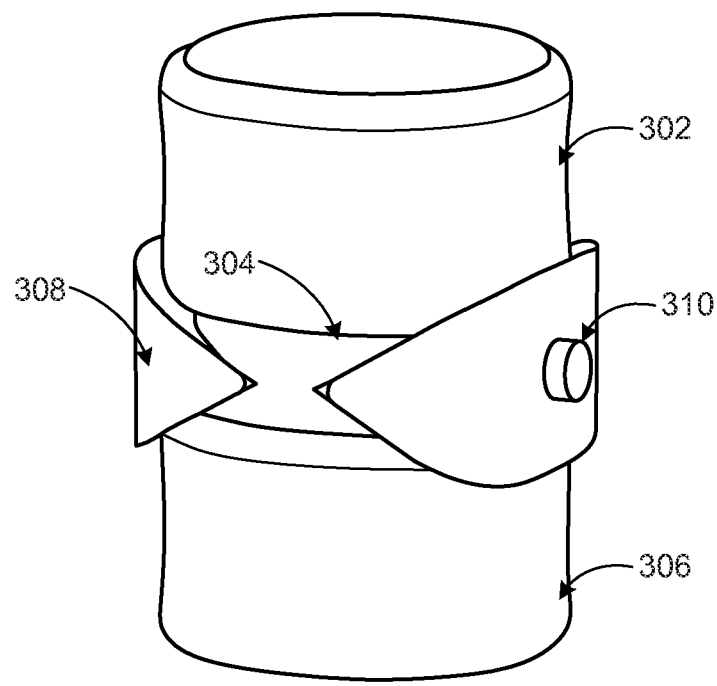
FIG. 3 illustrates example interbody fusion devices connected by an interconnecting member.

FIG. 3 illustrates example interbody fusion devices connected by an interconnecting member, arranged in accordance with at least some embodiments as described herein.

As discussed above an interbody fusion device may include two or more IVIs 308 inserted between adjacent vertebrae 302, 306. After insertion of the IVIs 308 in substantially opposite and parallel positions between the adjacent vertebrae 302, 306, the IVIs 308 may be connected together via an interconnecting member 310. The interconnecting member 310 may be a screw-type device exhibiting a thread, and the interconnecting member 310 may be positioned in a transverse orientation with respect to the vertebrae. The interconnecting member 310 may also be a rod, a wire suture, a braided material or other similar screw type device configured to transversely extend between the IVIs 308, and to provide dynamic and static stabilization. The interconnecting member 310 may pass through a portion of residual IVD 304 that remains after resection of the IVD. Additionally, the interconnecting member may be rigidly fixed to the IVIs, and may extend outside of the residual IVD. During resection of the IVD 304 to accommodate the IVIs 308, a perforation or resection may also be made through the IVD to accommodate the passage of the interconnecting member 310. Furthermore, a central recess may be formed in the IVD 304 to enable placement of autologous or allograft tissue and/or synthetic bone graft substitutes to promote bone formation to achieve bony bridging between the adjacent vertebrae via the central recess.

Additionally a distance between the first and second IVIs may be adjusted to increase a displacement between first and second vertebrae employing the interconnecting member. For example, the interconnecting member 310 may be exhibit a thread to enable the interconnecting member 310 to be rotated to reduce a distance between the IVIs 308 to draw the IVIs 308 closer together into a preferred position between the adjacent vertebrae 302, 306. Additionally, through the rotation of the interconnecting member 310 to reduce the distance between the IVIs 308, sloped recesses of the vertebrae may produce distraction of the IVD to achieve restoration of a disc height and preferred intervertebral spacing. In another example, the interconnecting member 310 connecting the IVIs may be deformable, such that a distance between them could be modified intraoperatively, and the spacing between the upper and lower VB's increased to the desired extent based on an induced deformation of the interconnecting member. After insertion of the interconnecting member 310 and positioning of the IVIs 308, the interconnecting member 310 may provide mechanical stabilization of the IVIs 308 to prevent translation and other movement of the IVIs 308 between the vertebrae 302, 306.

Figure 4A:
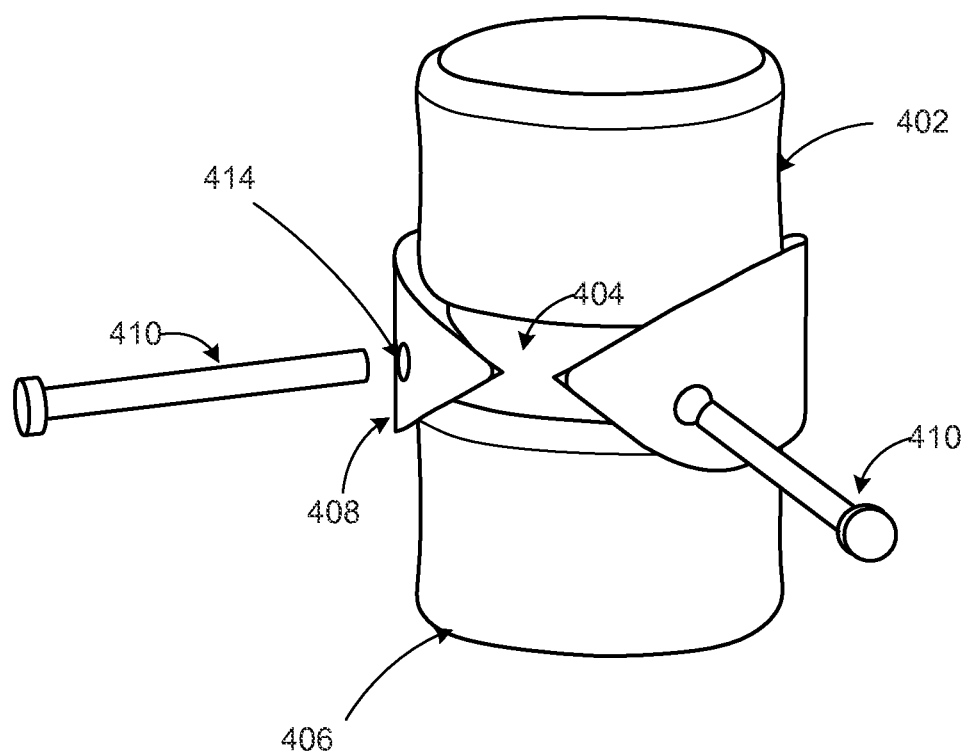
FIGS. 4A and 4B illustrate example interbody fusion devices connected by multiple interconnecting members.
Figure 4B:
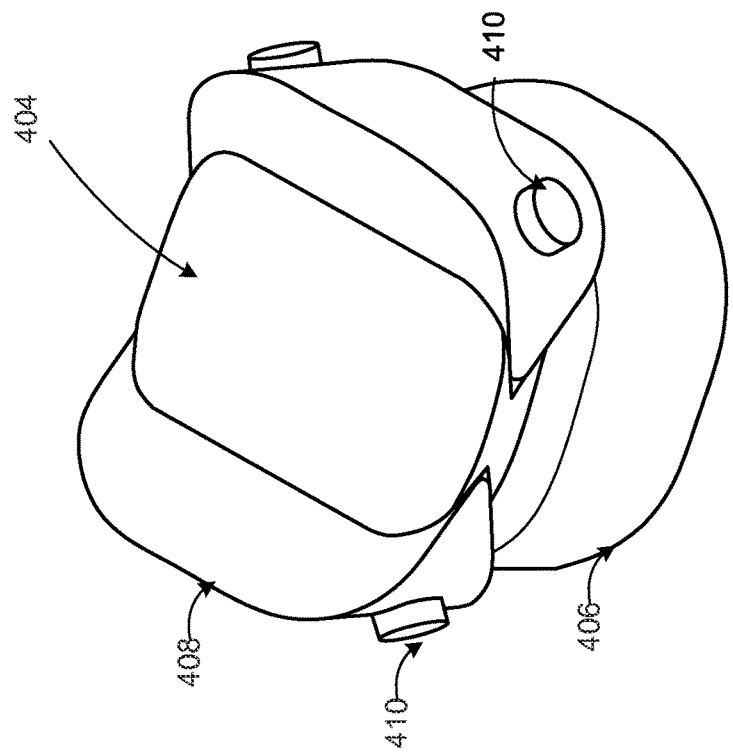
Figure 4B:
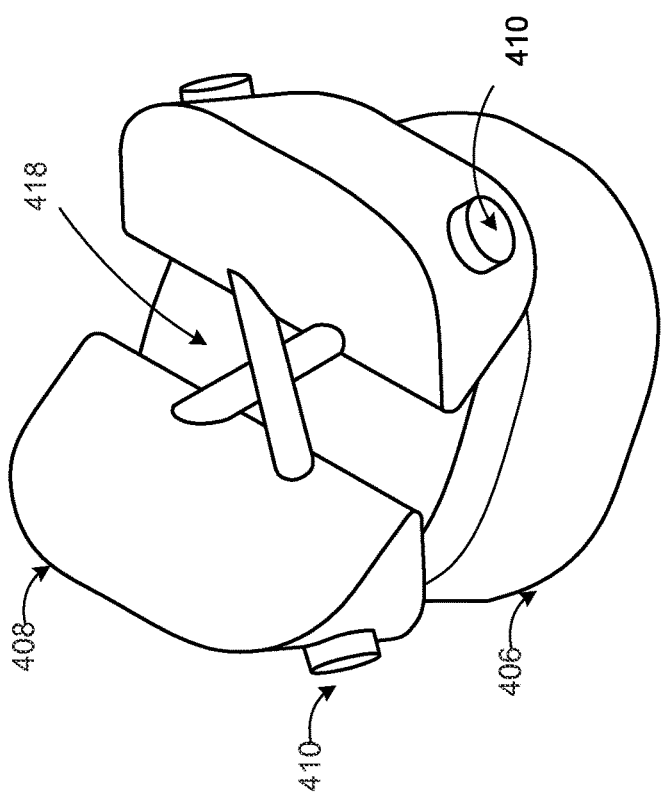

FIGS. 4A and 4B illustrate example interbody fusion devices connected by multiple interconnecting members, arranged in accordance with at least some embodiments as described herein.

In another example embodiment, two or more interconnecting members 410 may be employed together to position and stabilize IVIs 408 between adjacent vertebrae 402, 406. In an example, when two interconnecting members 410 are utilized together, the two interconnecting members 410 may be positioned in a cross-cruciate orientation 418 to provide mechanical constraint to relative movement of the IVIs 408. Corresponding perforations 414 may be made in the IVIs 408 and in the IVD 404 prior to insertion to accommodate insertion of the two interconnecting members 410 through the residual IVD. Employing two or more interconnecting members 410 together may provide additional mechanical stability in flexion, extension, lateral bending, and axial rotation motions of the spine.

In an example embodiment, the interconnecting member(s) 410 may be composed from various materials such as a metal material or a polymer material. Example metal materials may include a nickel-titanium alloy or a titanium alloy. The interconnecting member(s) 410 may also be composed from a polyetheretherketone (PEEK) material, or in other examples, the interconnecting member(s) 410 may also be composed a titanium alloy coated PEEK. Additionally, the interconnecting member(s) 410 may be composed from a bio-absorbable material to enable the interconnecting member(s) 410 to be resorbed by the body after permanent fusion between adjacent vertebrae has been achieved.

In an additional embodiment, in order to promote bony ingrowth and ongrowth to facilitate fusion, at least a portion of the interconnecting members 410 may be configured to be substantially porous to enable new bone growth between the vertebrae 402, 406 through the IVIs 408 and through the interconnecting member(s) 410. A bone graft, as previously described, may be integrated within the pores of the interconnecting member to promote bone growth through the interconnecting member. In another example embodiment, interconnecting members 410 may be configured to have a hollow center to promote bone growth between the vertebrae through the interconnecting member. A fusion by way of bone growth may be likely to occur in a radial dimension for the members. Bone graft may be inserted within the hollow center of the interconnecting member prior to insertion of the interconnecting member.

Figure 5:
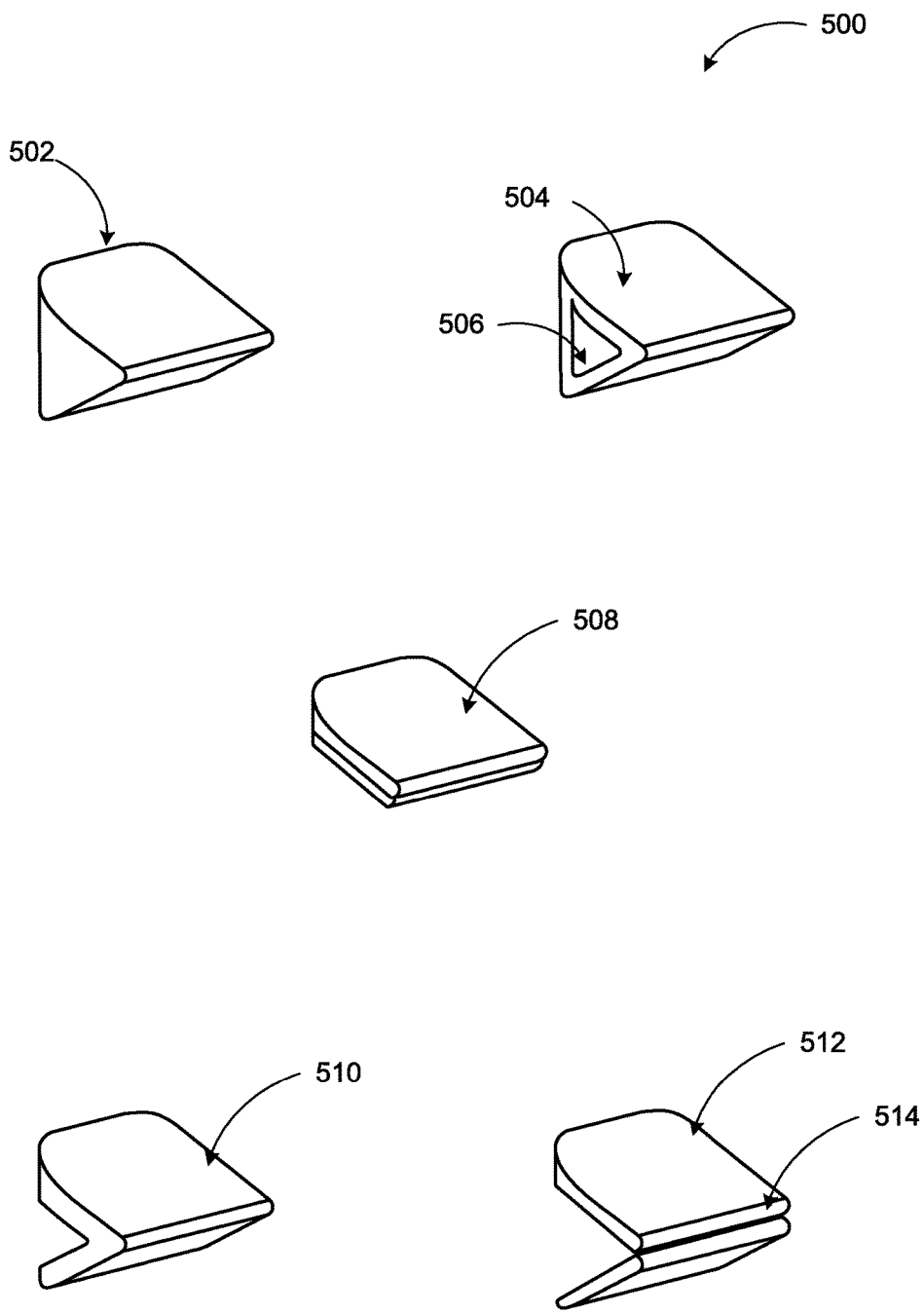
FIG. 5 illustrates various configurations of an interbody fusion device, all arranged in accordance with at least some embodiments as described herein.

FIG. 5 illustrates various configurations of an interbody fusion device, arranged in accordance with at least some embodiments as described herein.

As previously described, an interbody fusion device may include two or more wedge-shaped intervertebral implants (IVIs) configured to be inserted between adjacent vertebrae in substantially parallel and opposite orientations. In some example embodiments, the wedge-shaped IVIs may exhibit a solid uniform shape 502 such that a slope is constant from a thin end to a thick end of each IVI. In some examples, a uniform shaped IVI 504 may also have a hollow center 506 to enable insertion of bone graft while maintaining a rigid uniform shape.

In some other embodiments, the IVIs may exhibit other configurations to facilitate appropriate selection of IVIs based on various factors such as a patient's anatomy, race, gender, age, size, and level of disease. For example, the IVIs may be configured to be compliant or adjustable, such that the slope may be manipulated or changed after insertion. For example, the IVIs may be hinged to facilitate insertion of the IVIs in a compact or closed shape 508, and after insertion the IVIs may be opened 512 at the hinge 514 to increase the slope of the IVIs to a desired slope to achieve a preferred intervertebral distance. In another embodiment, the IVIs may be two-sided 510 with a hollow center to enable insertion of a bone graft, and to enable the IVIs to be slightly compliant when inserted between vertebrae. The example IVIs may allow some degree of motion, such as lateral bending and flexion extension of the functional unit (i.e. neighboring vertebrae) to which it is applied, once sufficient bony attachment has occurred. The allowed degree of motion may be further enhanced and controlled by modifying material properties and/or shape of the device. Other configurations are also possible to facilitate ease of access and insertion, and customizable selection of the IVIs for various patients and anatomies. For example, two opposite IVIs may be configured in a matching horseshoe design where ends of the horseshoes may point towards the midline of the disc.

While embodiments have been discussed above using specific examples, components, and configurations, they are intended to provide a general guideline to be used for providing an interbody spinal fusion device to achieve spinal fusion while maintaining intervertebral spacing. These examples do not constitute a limitation on the embodiments, which may be implemented using other components, modules, and configurations using the principles described herein. Furthermore, actions discussed above may be performed in various orders, especially in an interlaced fashion.

According to some examples, the present disclosure describes a spinal fusion device to achieve interbody fusion and maintain intervertebral spacing. The spinal fusion device may include a substantially wedge-shaped first intervertebral implant and a substantially wedge-shaped second intervertebral implant (IVI) configured to be inserted bilaterally between a first and second vertebrae displacing at least a portion of an intervertebral disk (IVD) between the first and second vertebrae. A thin end of each IVI may be positioned toward a midline of the first and second vertebrae. A thick end of each IVI may be positioned to be substantially flush with outer surfaces of the first and second vertebrae.

According to some examples, the first IVI and the second IVI may be additionally positioned substantially opposite and parallel to each other such that the thin ends may be positioned next to each other near a midline of the first and second vertebrae. According to some examples, the first IVI may be positioned at an anterior position between the first and second vertebrae and the second IVI may be positioned at a posterior position between the first and second vertebrae in relation to a midline of the vertebrae.

According to further examples, the first IVI may be positioned at a first lateral position between the first and second vertebrae and the second IVI may be positioned at a second lateral position between the first and second vertebrae in relation to a midline of the vertebrae. According to additional examples, a lateral cross section of upper surfaces of the first and second IVIs may be configured to match a lateral cross section of an inferior surface of the first vertebra and a lateral cross section of lower surfaces of the first and second IVIs, which may be configured to match a lateral cross section of a superior surface of the second vertebra.

According to some examples, a change in thickness from the thin end to the thick end of the first and second IVIs may be selected to match an anatomy of an intervertebral distance between the first and second vertebrae. According to further examples, a slope from the thin end to the thick end of the first and second IVIs may be selected to match an anatomy of a slope from an interior portion of the first and second VBs to an exterior portion of the first and second vertebrae.

According to further examples, a slope from the thin end to the thick end of the first and second IVIs may be selected to match a slope of a resected plane of the first and second vertebrae from an interior portion of the first and second vertebrae to an exterior portion of the first and second vertebrae. According to some examples, a slope of the first and second IVIs from anterior to a posterior position is modified in situ to match a desired kyphosis and/or lordosis of a spine such that the spinal fusion device exhibits a variable slope in two planes.

According to some examples, the slope from the thin end to the thick end of the first and second IVIs may be adjustable after insertion of the first and second IVIs between the first and second vertebrae to increase the intervertebral distance between the first and second vertebrae. According to some examples, the first and second IVIs may be composed from a metal material, a polymer material, a ceramic material, and/or a bio-absorbable material. According to further examples, the first and second IVIs may be composed from a porous material to promote bone growth between the first and second vertebrae through the first and second IVIs.

According to additional examples, a bone graft may be integrated with the porous first and second IVIs to promote bone growth between the first and second vertebrae through the first and second IVIs. According to further examples, the bone graft may be an autograft, an allograft, a bone graft substitute, and/or a bone morphogenic protein.

According to some examples, an upper surface and a lower surface of the first and second IVIs may be treated to create an osteoconductive surface to promote bone growth with the first and second IVIs. According to some examples, an upper surface and a lower surface of the first and second IVIs may be topographically treated to resist shear loading and expulsion.

According to additional examples, the spinal fusion device may further comprise an interconnecting member, which may be configured to connect the first IVI with the second IVI and may be configured to pass through a residual IVD to stabilize the first and second IVIs in position between the first and second vertebrae. According to additional examples, the interconnecting member may be one of: a rod or a wire suture configured to transversely extend between the first and second IVIs.

According to further examples, the interconnecting member may be threaded such that the interconnecting member is rotatable to reduce a distance between the first and second IVIs. According to further examples, the interconnecting member may be composed from one or more of: a metal material including nickel-titanium alloy and titanium alloy, a polyetheretherketone (PEEK) material, a polymer material, and a bio-absorbable material. According to some examples, at least a portion of the interconnecting member may be composed from a porous material to promote bone growth between the first and second vertebrae through the first and second IVIs and the interconnecting member.

According to some examples, a bone graft may be integrated within pores of the interconnecting member to promote bone growth between the first and second vertebrae through the interconnecting member. According to some examples, the interconnecting member may be configured to have a hollow center to promote bone growth between the first and second vertebrae through the interconnecting member.

According to additional examples, a bone graft may be inserted within the hollow center of the interconnecting member to promote bone growth between the first and second vertebrae through the interconnecting member.

According to some examples, the spinal fusion device may further comprise two interconnecting members configured to connect the first IVI with the second IVI and to pass through a residual IVD to stabilize the first and second IVIs in position between the first and second vertebrae.

According to further examples, the two interconnecting members may be positioned in a substantially cross cruciate orientation to provide mechanical constraint to relative movement of the first and second IVIs.

According to further examples, a plurality of IVIs, each being substantially wedge-shaped and tapered from a thick end to a thin end, may be configured to be inserted between the first and second vertebrae. The thin end of each IVI may be positioned toward a midline of the first and second vertebrae and the thick end of each IVI may be positioned to be substantially flush with outer surfaces of the first and second vertebrae.

According to some examples, the present disclosure describes a method to achieve interbody fusion. The method may include inserting first and second intervertebral implants (IVIs), each being substantially wedge-shaped and tapered from a thick end to a thin end, which may be between first and second vertebrae displacing at least a portion of an intervertebral disk (IVD) between the first and second vertebrae. The method may further include positioning the thin end of each IVI toward a midline of the first and second vertebrae such that the thick end of each IVI may be positioned to be substantially flush with outer surfaces of the first and second vertebrae.

According to some examples, the method may further comprise positioning the first IVI and second IVI in a substantially opposite and parallel position to each other such that the thin ends may be positioned next to each other near a midline of the first and second vertebrae.

According to further examples, the method may additionally comprise positioning the first IVI at an anterior position between the first and second vertebrae and positioning the second IVI at a posterior position between the first and second vertebrae in relation to a midline of the vertebrae.

According to additional examples, the method may further comprise positioning the first IVI at a first lateral position between the first and second vertebrae and positioning the second IVI at a second lateral position between the first and second vertebrae in relation to a midline of the vertebrae.

According to some examples, the method may further comprise inserting at least one interconnecting member configured to connect the first IVI with the second IVI and may be configured to pass through a residual IVD to stabilize the first and second IVIs in position between the first and second vertebrae. According to some examples, the method may further comprise rotating the interconnecting member to reduce a distance between the first and second IVIs.

According to additional examples, the method may further comprise integrating a bone graft with the interconnecting member to promote bone growth between the first and second vertebrae. According to some examples, the method may further comprise inserting a second interconnecting member in a substantially cross cruciate orientation with the first interconnecting member to provide mechanical constraint to relative movement of the first and second IVIs.

After insertion of the first IVI and the second IVI between the first and second vertebrae, the method may further include increasing the slope from the thin end to the thick end of the first IVI and the second IVI to increase an intervertebral distance between the first and second vertebrae.

According to further examples, the method may further comprise removing a portion of the IVD between the first and second vertebrae to accommodate insertion of the first and second intervertebral implants between the first and second vertebrae.

According to additional examples, the method may further comprise resecting a portion of the first and second vertebrae to accommodate insertion of the first IVI and the second IVI in intervertebral space between the first and second vertebrae.

According to some examples, the present disclosure describes a method of forming a spinal fusion device to achieve interbody fusion. The method may comprise configuring first and second intervertebral implants (IVIs) to have a substantially wedge-shape such that each IVI may be tapered from a thick end to a thin end. The first and second IVIs may be configured to be inserted between the first and second vertebrae, displacing at least a portion of an intervertebral disk (IVD) between the first and second vertebrae. The thin end of each IVI may be positioned toward a midline of the first and second vertebrae. The thick end of each IVI may be positioned to be substantially flush with outer surfaces of the first and second vertebrae.

The method may additionally comprise adapting at least one interconnecting member configured to connect the first IVI with the second IVI and to pass through a residual IVD to stabilize the first and second IVIs in position between the first and second vertebrae.

According to additional examples, the method may further comprise matching a lateral cross section of an upper surface of each of the first IVI and the second IVI with a lateral cross section of the inferior surface of the first vertebra. The method may further comprise matching a lateral cross section of the lower surface of each of the first IVI and the second IVI with a lateral cross section of the superior surface of the second vertebra.

According to some examples, the method may further comprise selecting a change in thickness from the thin end to the thick end of the first IVI and the second IVI to match an anatomy of an intervertebral distance between the first and second vertebrae.

According to further examples, the method may additionally comprise resecting a portion of the first and second VBs to accommodate insertion of the first and second IVIs in intervertebral space between the first and second vertebrae.

According to further examples, the method may additionally comprise configuring a slope from the thin end to the thick end of the first IVI and the second IVI to match a slope of a resected plane of the first and second vertebrae from an interior portion of the first and second vertebrae to an exterior portion of the first and second vertebrae.

According to some examples, the method may further comprise selecting a slope of the first and second IVIs from anterior to a posterior position in situ to match a desired kyphosis and/or lordosis of a spine such that the spinal fusion device exhibits a variable slope in two planes.

According to some examples, the method may additionally comprise composing the first and second IVIs from a polymer material, a ceramic material, and/or a bio-absorbable material.

According to additional examples, the method may comprise composing the first and second IVIs from a porous material for promoting bone growth between the first and second vertebrae through the IVI.

According to some examples, the method may comprise integrating a bone graft within the porous first and second IVIs to promote bone growth between the first and second vertebrae through the first and second IVIs.

According to some examples, the method may further comprise selecting the bone graft from an autograft, an allograft, a bone graft substitute, and/or a bone morphogenic protein.

According to some examples, the method may further comprise treating an upper surface and a lower surface of the first and second IVIs to create an osteoconductive surface to promote bone growth with the first and second IVIs. According to additional examples, the method may further comprise topographically treating an upper surface and a lower surface of the first and second IVIs to resist shear loading and expulsion.

According to some examples, the method may further comprise selecting the interconnecting member from a rod or a wire suture. According to some examples, the method may also comprise composing the interconnecting member from one or more of: a metal material including nickel-titanium alloy and titanium alloy, a polyetheretherketone (PEEK) material, a polymer material, and a bio-absorbable material.

According to some examples, the method may further comprise composing at least a portion of the interconnecting member from a porous material to promote bone growth between the first and second vertebrae through the first and second IVIs and the interconnecting member. According to additional examples, the method may further comprise integrating a bone graft within pores of the interconnecting member to promote bone growth between the first and second vertebrae through the interconnecting member.

According to additional examples, the method may comprise configuring the interconnecting member to have a hollow center to promote bone growth between the first and second vertebrae through the interconnecting member. The method may also comprise inserting a bone graft within the hollow center of the interconnecting member to promote bone growth between the first and second vertebrae through the interconnecting member.

According to some examples, the present disclosure describes a system for achieving interbody fusion. The system may comprise a substantially wedge-shaped first intervertebral implant and a substantially wedge-shaped second intervertebral implant (IVI) configured to be inserted bilaterally between a first and second vertebrae displacing at least a portion of an intervertebral disk (IVD) between the first and second vertebrae, where a thin end of each IVI may be positioned toward a midline of the first and second vertebrae and a thick end of each IVI may be positioned to be substantially flush with outer surfaces of the first and second vertebrae. The system may also comprise an interconnecting member configured to connect the first IVI with the second IVI and to pass through the residual IVD to stabilize the first and second IVIs in position between the first and second vertebrae.

According to some examples, the first IVI and the second IVI may be positioned substantially opposite and parallel to each other such that the thin ends may be positioned next to each other near a midline of the first and second vertebrae.

According to additional examples, a lateral cross section of upper surfaces of the first and second IVIs may be configured to match a lateral cross section of an inferior surface of the first vertebra and a lateral cross section of lower surfaces of the first and second IVIs may be configured to match a lateral cross section of a superior surface of the second vertebra.

According to further examples, a change in thickness from the thin end to the thick end of the first and second IVIs may be selected to match an anatomy of an intervertebral distance between the first and second vertebrae.

According to some examples, a slope of the first and second IVIs from anterior to a posterior position is modified in situ to match a desired kyphosis and/or lordosis of a spine such that the spinal fusion device exhibits a variable slope in two planes.

According to further examples, the first and second IVIs may be composed from one or more of: a polymer material, a ceramic material, a bio-absorbable material. According to some examples, the first and second IVIs may be composed from a porous material for promoting bone growth between the first and second vertebrae through the first and second IVIs.

According to some examples, a bone graft may be integrated with the porous first and second IVIs to promote bone growth between the first and second vertebrae through the first and second IVIs. According to further examples, the bone graft may be one or more of: an autograft, an allograft, a bone graft substitute, and a bone morphogenic protein.

According to further examples, the interconnecting member may be a rod configured to transversely extend between the first and second IVIs. According to some examples, the interconnecting member may be threaded such that the interconnecting member can be rotated to reduce a distance between the first and second IVIs.

According to some examples, the interconnecting member may be composed from one or more of: a metal material including nickel-titanium alloy and titanium alloy, a polyetheretherketone (PEEK) material, a polymer material, and a bio-absorbable material. According to some examples, at least a portion of the interconnecting member may be composed from a porous material to promote bone growth between the first and second vertebrae through the first and second IVIs and the interconnecting member.

According to additional examples, a bone graft may be integrated within pores of the interconnecting member to promote bone growth between the first and second vertebrae through the interconnecting member. According to some examples, the interconnecting member may be configured to have a hollow center to promote bone growth between the first and second vertebrae through the interconnecting member. According to some examples, a bone graft may be inserted within the hollow center of the interconnecting member to promote bone growth between the first and second vertebrae through the interconnecting member.

According to additional examples, two interconnecting members may be configured to connect the first IVI with the second IVI and to pass through the residual IVD to stabilize the first and second IVIs in position between the first and second vertebrae. According to further examples, the two interconnecting members may be positioned in a substantially cross cruciate orientation to provide mechanical constraint to relative movement of the first and second IVIs.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected," or "operably "coupled," to each other to achieve the desired functionality, and any two components capable of being so associated may also be viewed as being "operably couplable," to each other to achieve the desired functionality. Specific examples of operably couplable include but are not limited to physically connectable and/or physically interacting components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A spinal fusion device to achieve interbody fusion and maintain intervertebral spacing, the spinal fusion device comprising:
a substantially wedge-shaped first intervertebral implant and a substantially wedge-shaped second intervertebral implant (IVI) configured to be inserted bilaterally between a first vertebra and a second vertebra, and to displace at least a portion of an intervertebral disk (IVD) between the first and second vertebrae, wherein a thin end of each IVI is configured to be positioned toward a midline of the first and second vertebrae and a thick end of each IVI is configured to be positioned to be substantially flush with outer surfaces of the first and second vertebrae, wherein a slope from the thin end to the thick end of the first and second IVIs is adjustable after insertion of the first and second IVIs between the first and second vertebrae to increase an intervertebral distance between the first and second vertebrae.

2. The spinal fusion device of claim 1, wherein the first IVI and the second IVI are configured to be positioned substantially opposite and parallel to each other such that the thin ends are configured to be positioned next to each other near a midline of the first and second vertebrae.

3. The spinal fusion device of claim 1, wherein the first IVI is configured to be positioned at an anterior position between the first and second vertebrae and the second IVI is configured to be positioned at a posterior position between the first and second vertebrae in relation to a midline of the vertebrae.

4. The spinal fusion device of claim 1, wherein the first IVI is configured to be positioned at a first lateral position between the first and second vertebrae and the second IVI is configured to be positioned at a second lateral position between the first and second vertebrae in relation to a midline of the vertebrae.

5. The spinal fusion device of claim 1, wherein a lateral cross section of upper surfaces of the first and second IVIs is configured to match a lateral cross section of an inferior surface of the first vertebra and a lateral cross section of lower surfaces of the first and second IVIs is configured to match a lateral cross section of a superior surface of the second vertebra.

6. The spinal fusion device of claim 1, wherein a change in thickness from the thin end to the thick end of the first and second IVIs is selected to match an anatomy of an intervertebral distance between the first and second vertebrae.

7. The spinal fusion device of claim 1, wherein the slope from the thin end to the thick end of the first and second IVIs is selected to match an anatomy of a slope from an interior portion of the first and second vertebrae to an exterior portion of the first and second vertebrae.

8. The spinal fusion device of claim 1, wherein the slope from the thin end to the thick end of the first and second IVIs is selected to match a slope of a resected plane of the first and second vertebrae from an interior portion of the first and second vertebrae to an exterior portion of the first and second vertebrae.

9. The spinal fusion device of claim 1, wherein a slope of the first and second IVIs from anterior to a posterior position is capable of being modified to match a desired kyphosis and/or lordosis of a spine.

10. The spinal fusion device of claim 1, wherein the first and second IVIs are composed from one or more of: a metal material, a polymer material, a ceramic material, and a bio-absorbable material.

11. A method to achieve interbody fusion, the method comprising:
inserting first and second intervertebral implants (IVIs), each being substantially wedge-shaped and tapered from a thick end to a thin end, between first and second vertebrae displacing at least a portion of an intervertebral disk (IVD) between the first and second vertebrae; and
positioning the thin end of each IVI toward a midline of the first and second vertebrae such that the thick end of each IVI is positioned to be substantially flush with outer surfaces of the first and second vertebrae, wherein a slope from the thin end to the thick end of the first and second IVIs is adjustable after insertion of the first and second IVIs between the first and second vertebrae to increase an intervertebral distance between the first and second vertebrae.

12. The method of claim 11, further comprising:
positioning the first IVI and second IVI in a substantially opposite and parallel position to each other such that the thin ends are positioned next to each other near a midline of the first and second vertebrae.

13. The method of claim 11, further comprising:
inserting at least one interconnecting member configured to connect the first IVI with the second IVI and to pass through a residual IVD to stabilize the first and second IVIs in position between the first and second vertebrae.

14. The method of claim 13, further comprising:
reducing a distance between the first and second IVIs to increase a displacement between first and second vertebrae.

15. The method of claim 13, further comprising:
integrating a bone graft with the interconnecting member to promote bone growth between the first and second vertebrae.

16. A system for achieving interbody fusion, the system comprising:
a substantially wedge-shaped first intervertebral implant and a substantially wedge-shaped second intervertebral implant (IVI) configured to be inserted bilaterally between a first and second vertebrae displacing at least a portion of an intervertebral disk (IVD) between the first and second vertebrae, wherein a thin end of each IVI is configured to be positioned toward a midline of the first and second vertebrae and a thick end of each IVI is configured to be positioned to be substantially flush with outer surfaces of the first and second vertebrae; and
an interconnecting member configured to connect the first IVI with the second IVI and to pass through the residual IVD to stabilize the first and second IVIs in position between the first and second vertebrae, wherein a slope from the thin end to the thick end of the first and second IVIs is adjustable after insertion of the first and second IVIs between the first and second vertebrae to increase an intervertebral distance between the first and second vertebrae.

17. The system of claim 16, wherein the first and second IVIs are composed from a porous material for promoting bone growth between the first and second vertebrae through the first and second IVIs, and wherein a bone graft is integrated with the porous first and second IVIs to promote bone growth between the first and second vertebrae through the first and second IVIs.

18. The system of claim 17, wherein the bone graft is one or more of: an autograft, an allograft, a bone graft substitute, and a bone morphogenic protein.

19. The system of claim 16, wherein at least a portion of the interconnecting member is composed from a porous material to promote bone growth between the first and second vertebrae through the first and second IVIs and the interconnecting member.

\* \* \* \* \*

UNITED STATES PATENT AND TRADEMARK OFFICE
CERTIFICATE OF CORRECTION

PATENT NO. : 9,855,149 B2
APPLICATION NO. : 14/488910
DATED : January 2, 2018
INVENTOR(S) : Bertollo et al.

Page 1 of 1

It is certified that error appears in the above-identified patent and that said Letters Patent is hereby corrected as shown below:

In the Specification

In Column 8, Line 52, delete "insertion the" and insert -- insertion, the --, therefor.

Signed and Sealed this
Twenty-fourth Day of April, 2018

Andrei Iancu
*Director of the United States Patent and Trademark Office*